US009063107B2

(12) United States Patent
Waterbury et al.

(10) Patent No.: US 9,063,107 B2
(45) Date of Patent: Jun. 23, 2015

(54) APPARATUS, SYSTEMS, AND METHODS ADAPTED TO RINSE AND DRY CLINICAL ANALYZER SAMPLE PROBES

(75) Inventors: Raymond Waterbury, Mirabel (CA); Antoine Elias Haddad, Newark, DE (US); John Paul Mizzer, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 467 days.

(21) Appl. No.: 13/510,840

(22) PCT Filed: Nov. 17, 2010

(86) PCT No.: PCT/US2010/057021
§ 371 (c)(1),
(2), (4) Date: May 18, 2012

(87) PCT Pub. No.: WO2011/062982
PCT Pub. Date: May 26, 2011

(65) Prior Publication Data
US 2012/0227771 A1 Sep. 13, 2012

Related U.S. Application Data

(60) Provisional application No. 61/263,075, filed on Nov. 20, 2009.

(51) Int. Cl.
| B08B 5/00 | (2006.01) |
| B08B 5/02 | (2006.01) |
| B08B 9/00 | (2006.01) |
| B08B 9/02 | (2006.01) |
| G01N 35/10 | (2006.01) |

(52) U.S. Cl.
CPC .................. G01N 35/1004 (2013.01)

(58) Field of Classification Search
CPC ............ B08B 5/00; B08B 5/02; B08B 5/023; B08B 3/047; B08B 9/00; B08B 9/02; B08B 9/0321; B08B 9/0328; B08B 9/0913; G01N 35/1004; G01N 35/1009

USPC .......... 134/21, 22.1, 22.11, 22.12, 30, 31, 37, 134/95.1, 95.2, 102.1, 102.2
See application file for complete search history.

(56) References Cited

U.S. PATENT DOCUMENTS

| 3,957,639 | A | * | 5/1976 | Schoen et al. ............... 210/107 |
| 4,166,305 | A | * | 9/1979 | Gustafsson ................. 15/302 |
| 5,603,342 | A | | 2/1997 | Shambaugh |
| 5,827,744 | A | * | 10/1998 | Fose et al. ..................... 436/49 |
| 2008/0099057 | A1 | | 5/2008 | Dunfee et al. |

FOREIGN PATENT DOCUMENTS

| EP | 0725279 | * | 8/1996 |
| EP | 0725279 A1 | | 8/1996 |

OTHER PUBLICATIONS

Chinese Office Action of corresponding Chinese patent Application No. 201080052342.8, 21 Pages.

* cited by examiner

Primary Examiner — Saeed T Chaudhry
(74) Attorney, Agent, or Firm — Dugan & Dugan, PC

(57) ABSTRACT

A rinsing and drying apparatus of a clinical analyzer probe drain station is provided. The rinsing and drying apparatus has a group of nozzles that are offset from a longitudinal axis of a probe passage and may be inclined and oriented to provide tangentially oriented fluid-jet trajectories exiting into the sample probe passage. The offset nozzles, nozzle orientation, and cavity geometrical features of the device permit the drying capacity of probe-impinging planar air-knife jets to be maximized by stabilizing local internal fluid movement to form a swirling (e.g., helical) gas flow field directed away from a drying region and toward a vacuum exhaust. The rinsing and drying apparatus eliminates rinse water re-circulated entrainment and up-wash (spitting) during the air-knife drying operation. Therefore, the rinsing and drying apparatus significantly reduces water carryout on sampling probes thereby reducing sample/reagent dilution.

20 Claims, 15 Drawing Sheets

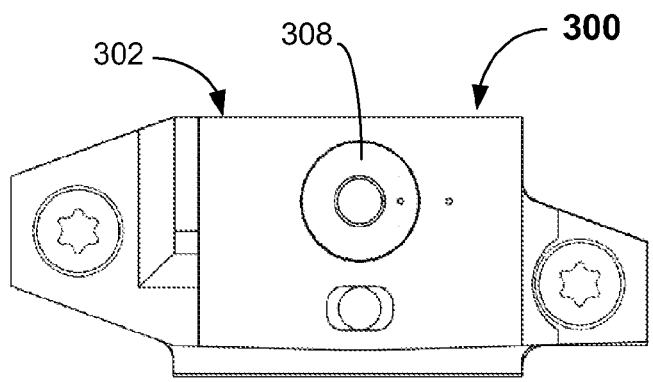
FIG. 3J
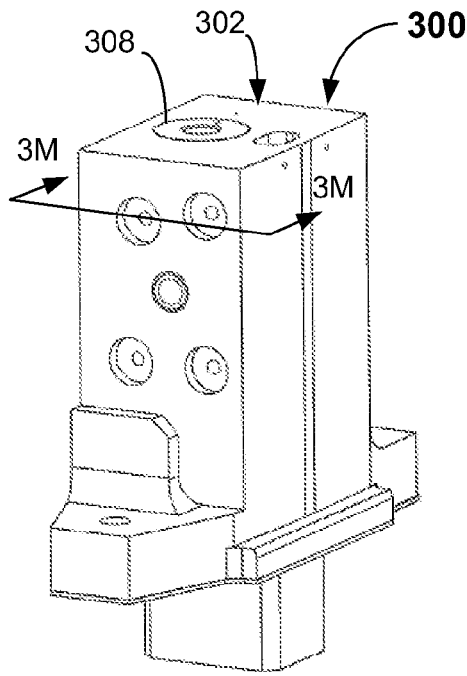 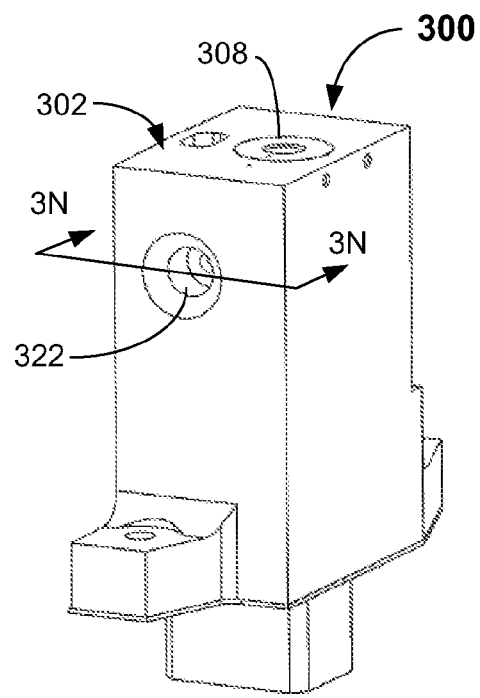
FIG. 3K  FIG. 3L

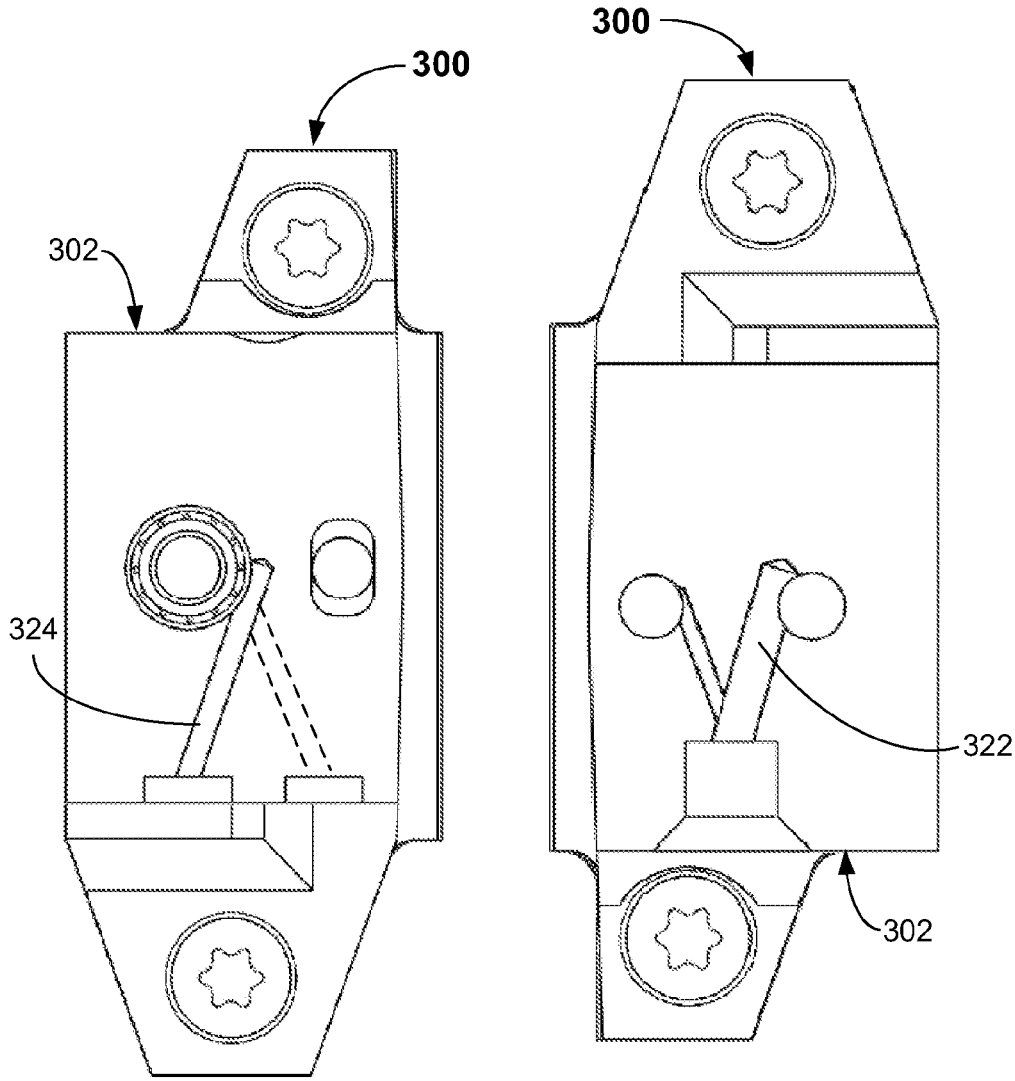
*FIG. 3M*  *FIG. 3N*

APPARATUS, SYSTEMS, AND METHODS ADAPTED TO RINSE AND DRY CLINICAL ANALYZER SAMPLE PROBES

RELATED APPLICATIONS

This application claims priority to U.S. Provisional Application Ser. No. 61/263,075 entitled "PROBE EXTERIOR RINSE AND DRYING DEVICE FOR A CLINICAL ANALYZER" filed on Nov. 20, 2009, the disclosure of which is hereby incorporated by reference in its entirety herein.

FIELD OF THE INVENTION

The present invention relates generally to apparatus, systems, and methods adapted for rinsing and drying of sample probes in clinical chemical analyzers.

BACKGROUND

Handling of liquid samples, reagents, and other liquids is an essential part of the implementation of automated clinical chemistry test methods. Precision sample probes are used to aspirate and/or dispense these liquids in conventional clinical chemistry analyzers. For economy, sample probes are reused. Accordingly, sample probes are automatically cleansed, rinsed, and dried at a cleansing and rinsing station (a.k.a. a drain station) within conventional clinical chemistry analyzers. This is intended to limit an extent of carry-over of a previous sample and/or reagent artifacts ("carry-over") or carry-over of rinse water that may dilute samples and/or reagents ("dilution"). Such carry-over and/or dilution may affect an accuracy of the clinical tests being performed on a sample.

The tasks carried out by a conventional chemical analyzer drain station are: (1) to clean and rinse the sample probe(s) that will be used to access the sample and/or reagent so as to minimize carry-over, and thereafter (2) to dry the sample probe(s) to make the sample probe(s) ready for reuse on a next sample or next sample test sequence.

Improvement of the effectiveness of such drain stations may improve the accuracy of tests performed by the clinical chemistry analyzer. Accordingly, there is a need to improve the effectiveness of the cleansing, rinsing, and drying processes carried out by clinical chemistry analyzer drain stations.

SUMMARY

In one aspect, the present invention provides a sample probe rinsing and drying apparatus. The sample probe rinsing and drying apparatus includes a drain station body defining a rinsing well adapted to contain a rinsing liquid, and defining a nozzle recess; and a nozzle insert received in the nozzle recess to form a first annulus, the nozzle insert having a probe passage formed along a longitudinal axis, the probe passage adapted to receive the sample probe therein, and at least two nozzles having entries at the first annulus and exits at the probe passage, each of the at least two nozzles having a central axis that is offset from the longitudinal axis.

According to another aspect, the present invention provides a sample probe rinsing and drying system. The system includes a pressurized fluid source; a drain station body defining a rinsing well and nozzle recess; and a nozzle insert received in the nozzle recess to form a first annulus, the nozzle insert having a probe passage formed along a longitudinal axis adapted to receive a sample probe therein, and at least two nozzles having entries at the first annulus and exits at the probe passage, each of the at least two nozzles being oriented and configured to direct a flow of fluid into the probe passage, wherein a portion of each flow of fluid from the nozzles contacts the probe and the remaining portions of each flow of fluid together form a substantially helical flow field within the probe passage.

In another aspect, the present invention provides a method of rinsing and drying a sample probe. The rinsing and drying method includes lowering the sample probe through a probe passage and into a rinsing well; providing a substantially helical flow of fluid to the probe passage and around the sample probe; and withdrawing the sample probe from the rinsing well wherein rinsing liquid is removed from the sample probe by gas jet impingement and the substantially helical flow.

According to another method aspect, a method of rinsing and drying a sample probe is provided. The rinsing and drying method includes lowering the sample probe along a longitudinal axis of a probe passage and into a rinsing well including rinsing liquid; providing a flow of fluid into a substantially cylindrical annulus surrounding the probe passage; directing the flow of fluid from the substantially cylindrical annulus through at least two nozzles and into the probe passage and around the sample probe wherein the flow of fluid from each of the at least two nozzles has a central axis that is offset from the longitudinal axis relative to a horizontal axis coincident with the longitudinal axis; and withdrawing the sample probe from the rinsing well wherein the rinsing liquid is removed from the sample probe by impingement and gas-jet wiping by a substantially helical flow created by the offset.

Still other aspects, features, and advantages of the present invention may be readily apparent from the following detailed description illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

BRIEF DESCRIPTION OF THE DRAWINGS

The invention will be better understood by referring to the detailed description taken in conjunction with the following drawings.

FIG. 3J is a top plan view diagram of a rinsing and drying apparatus according to embodiments of the present invention.

FIGS. 3K and 3L are left and right side perspective views, respectively, of the embodiment of rinsing and drying apparatus of FIG. 3J according to the present invention.

FIGS. 3M and 3N are cross-sectioned top views of the rinsing and drying apparatus taken along section lines "3M-3M" and "3N-3N" of FIGS. 3K and 3L, respectively.

DETAILED DESCRIPTION

In view of the foregoing difficulties and propensity for inaccurate results due to possible carry-over and/or dilution, there is an unmet need to improve the effectiveness of existing rinsing and drying apparatus and systems (drain stations) in terms of effectiveness of rinsing and/or drying of a sample probe. To address this need, embodiments according to aspects of the present invention provide improved nozzles, improved rinsing and drying apparatus, improved sample probe rinsing and drying systems, and improved rinsing and drying methods. The rinsing and drying apparatus and system may improve dilution by up to about 15 times, and may improve results' precision by at least about 2 times as compared to prior clinical chemistry analyzers.

Figure 1:
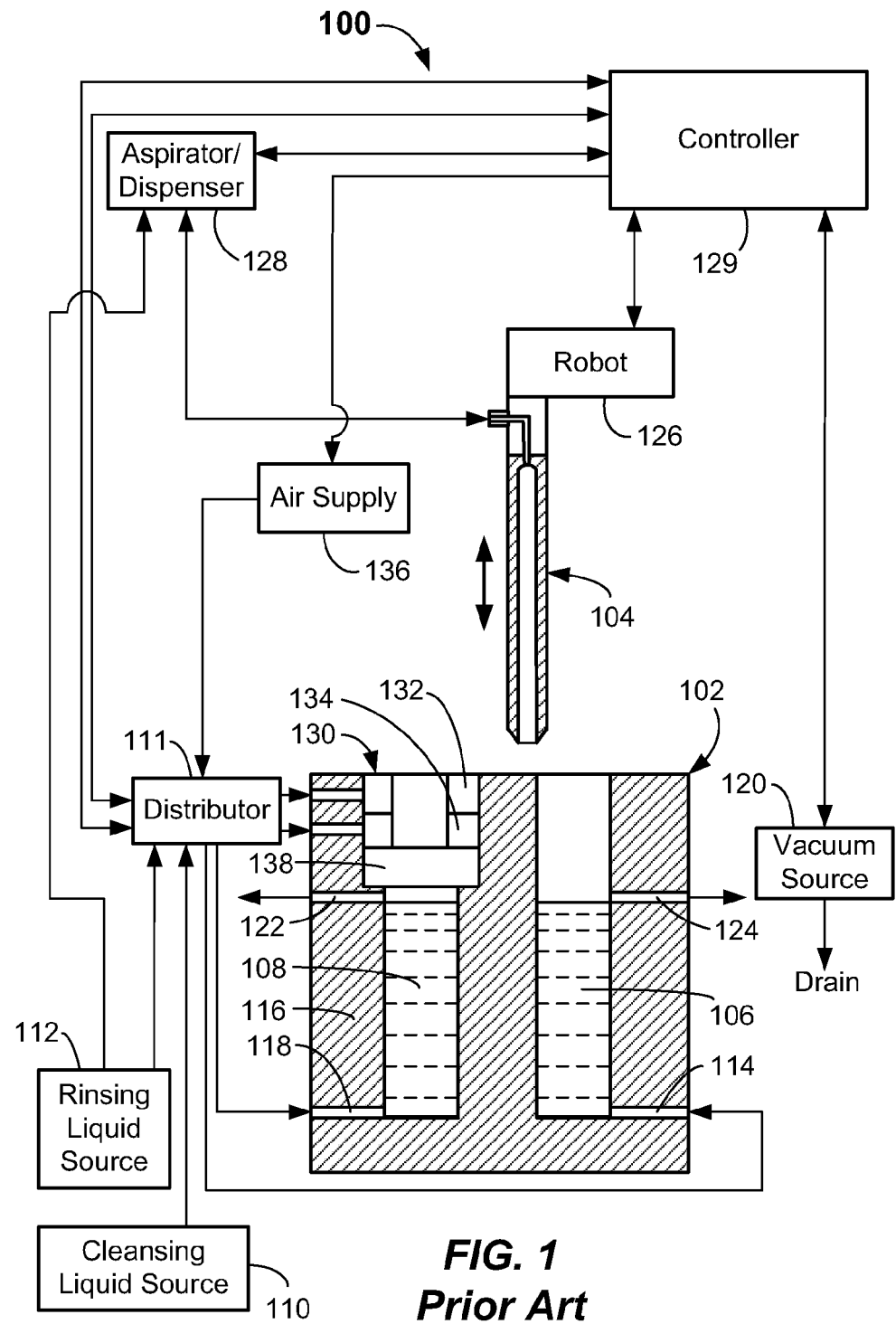
FIG. 1 is a partially cross-sectioned side plan view diagram of a sample probe rinsing and drying system according to the prior art.

FIG. 1 illustrates a portion of a clinical analyzer 100 according to the prior art that includes a conventional rinsing and drying apparatus 102 (otherwise referred to as a "drain station"). The rinsing and drying apparatus 102 has two locations for the probe 104 to enter, namely a cleansing well 106 and the rinsing well 108. Each well 106, 108 is bottom-fed from respective cleansing liquid source 110 and rinsing liquid source 112. Cleansing liquid is supplied to cleansing well 106 from the cleansing liquid source 110 through distributor 111 and passage 114 formed in the drain station body 116 to provide a static cleansing bath. Rinsing liquid is supplied to the rinsing well 108 from rinsing liquid source 112 through distributor 111 and passage 118 to provide a rinsing bath. A vacuum overflow feature is provided that maintains predetermined fluid height within the wells 106, 108, removes waste, and exhausts all air and liquid entering the wells 106, 108. A suitable vacuum source 120 is coupled to (coupling is not shown) exhaust ports 122, 124 interfacing with each of the wells 106, 108 at a predetermined well height and carries the exhausted liquids, other materials, and air to a drain.

The cleansing well 106 may typically hold either sodium hypochlorite or sodium hydroxide cleaning liquids, and the rinsing well 108 may hold water. A robot 126 causes the sample probe 104 to move in two or more coordinate directions (e.g., vertical and horizontal). Accordingly, the probe 104 may aspirate sample, reagent, or other liquid at a first location with an aspirator/dispenser unit 128 and move the sample, reagent, or other liquid contained in the probe 104 to a second location and dispense the sample, reagent, or other liquid. Optionally, or in addition, rinsing liquid from the rinsing liquid source 112 may be dispensed by the aspirator/dispenser 128 through the sample probe 104 to rinse an interior of the sample probe 104.

At the top end of the rinsing well 108, a nozzle assembly 130 is provided. The nozzle assembly 130 has two sets of nozzle features therein. The features are an air-knife feature 132 and a shower feature 134. The nozzle features 132, 134 direct multiple air and water jets to wash and dry the sample probe 104 received in the rinsing well 108, respectively. The geometry and structure of the nozzle features 132, 134 of a conventional nozzle coupled with the geometry of the rinsing well 108 of the rinsing and drying apparatus 102 produces a high degree of turbulent recirculation. Consequently, this results in unpredictable behavior of water droplet trajectories and water droplet deposition onto the surface of the sample probe 104 during the process of withdrawing and drying the probe 104 after rinsing well immersion.

The rinsing and drying apparatus 102 functions within the following typical sequence. The sample probe 104 is lowered by robot 126 into the cleansing well 106 to soak the exterior surfaces thereof. Cleansing solution may be aspirated by aspirator/dispenser 128 into the probe 104 to soak the interior surfaces of the probe 104. The probe 104 is withdrawn from the cleansing well 106 by robot 126 and repositioned over the rinsing well 108. The probe 104 is lowered by robot 126 into the rinsing well 108. The probe 104 and the upper section of the rinse well 108 may be showered with water (via shower feature 134) from rinsing liquid source 112. Rinsing solution may be flushed through the interior of the probe 104 using aspirator/dispenser 128. Rinsing solution is pumped into the bottom of the rinsing well 108 to flush and replenish the static rinsing bath. The probe 104 is withdrawn by robot 126 from the rinsing well 108 while the air-knife jets attempt to wipe away remaining water droplets from the outer surface of the probe 104 (via air-knife feature 132).

Figure 2A:
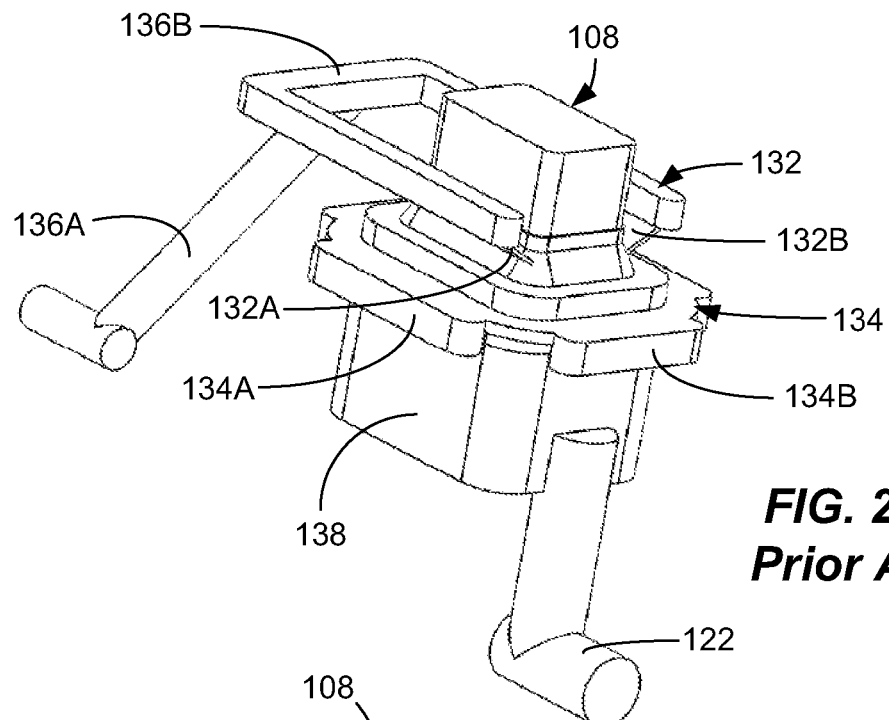
FIG. 2A is a perspective view diagram of the fluid-containing passages and cavities of a sample probe rinsing and drying apparatus according to embodiments of the prior art.
Figure 2B:
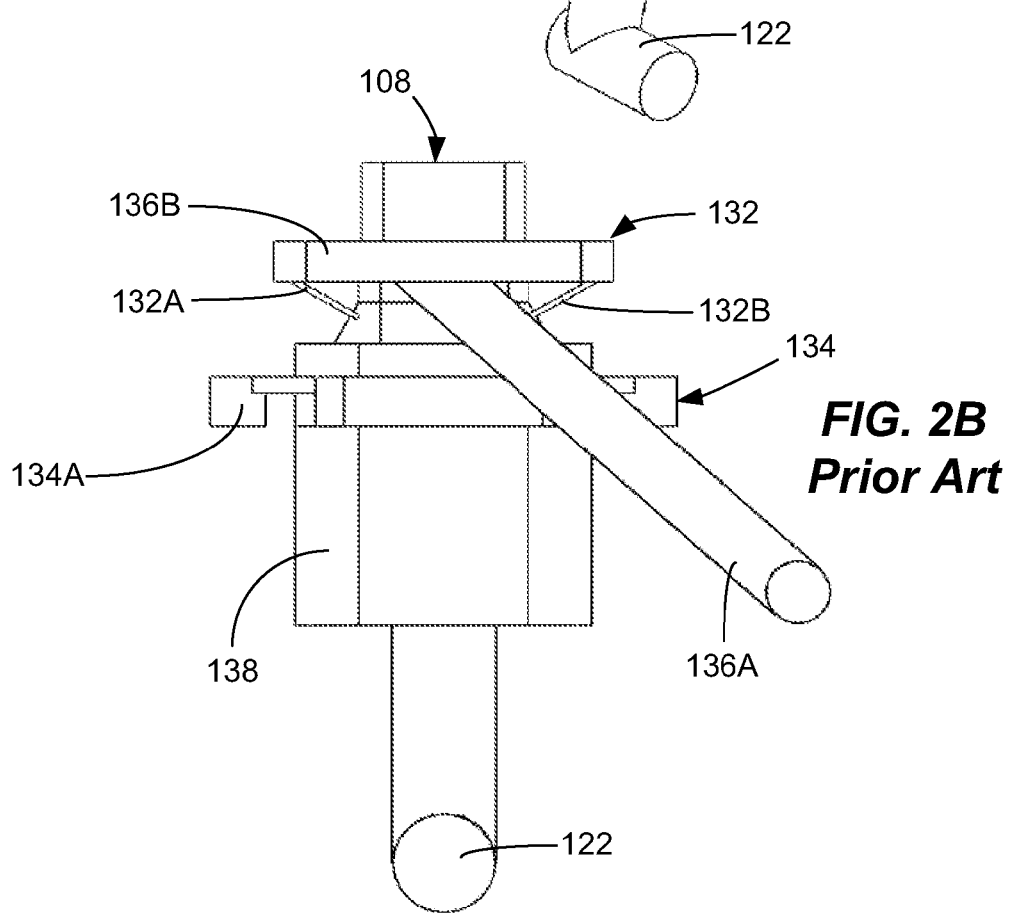
FIG. 2B is a side view diagram of the fluid-containing passages and cavities of the sample probe rinsing and drying apparatus of FIG. 2A according to embodiments of the prior art.

However, the inventors herein have discovered that rinsing liquid "carryout" and "spitting" effects occur in the operation of such conventional rinsing and drying apparatus and systems. Such effects are a consequence of the turbulence induced by internal cavity geometry of the rinsing well 108, as well as air-jet nozzle design and configuration. FIGS. 2A and 2B illustrate the geometry of the cavities and fluid-containing passages of the shower feature 134 and the air-knife feature 132 with the body 116 not being shown for clarity. Passages 136A, 136B provide air from an air supply 136 (FIG. 1) to the air-knife feature 132. The air-knife feature 132 includes a first air knife 132A and a second air knife 132B positioned at the right and left sides of the upper portion of the rinsing well 108. The rectangular-shaped reservoir 138 of the rinsing well 108 includes a generally rectangular cross section at various horizontal cross-sections thereof. The first air knife 132A and second air knife 132B are oriented to pass respective opposing planar air jets onto the exterior surface of the probe 104 as the probe 104 is withdrawn from the upper portion 138 of the rinsing well 108 by the robot 126. This is intended to strip away any rinsing liquid or sample material remaining on the sample probe 104. However, as will be seen below, this stripping action may be less then optimal.

Shower feature 134 is positioned below the air-knife feature 132 and includes generally-orthogonal passages 134A, 134B, etc. that generally surround the upper portion of the rinsing well 108. The shower feature 134 is operable to spray jets of water from a plurality of rinse jet passages positioned in fluid communication with the passages 134A, 134B, etc. onto the exterior surface of the probe 104 and onto the interior of the rectangular-shaped reservoir 138 of the rinsing well 108. The rinsing liquid is collected into a rectangular-shaped reservoir 138 of the rinsing well 108 that is located below the shower feature 134. The rinsing liquid ejected from the shower feature 134 and any material removed from the probe 104 is evacuated through the vacuum exhaust port 122.

During the idle mode of operation when the shower feature 134 and air-knife feature 132 are not operating and only flow to the vacuum port 122 is provided, air entering the sudden expansion of the rectangular-shaped reservoir 138 of the rinsing well 108 from atmosphere re-circulates in the rectangular-shaped reservoir 138, principally as a pair of large, standing, counter-rotating vortices. These counter-rotating vortices entrain any remaining water from the well walls, shower feature 134, and the rinsing well bath of the rectangular-shaped reservoir 138 of the rinsing well 108. This effect is amplified when the air-knife feature 132 is operable due to the increased volumetric air flow and velocity from the two opposed, inclined planar air-knife jets used to dry the sample probe 104. Moreover, as the sample probe 104 is withdrawn, the air-knife jets may merge; directly impacting the surface of the rinsing well static bath to create an up-wash of rinsing liquid (e.g., water) into the vertical flow field. This liquid is propelled into the underside of the jets of the air-knife feature 132 and then onto the probe 104. These fluid flow dynamics lead to a high propensity for ejection of rinsing liquid droplets from the drain system (spitting), carryout of the rinsing liquid on the probe 104, and, consequently, sample and/or reagent dilution and propensity for less accurate analytical results because of such dilution.

Thus, there remains a need for a structure of a rinsing and drying apparatus (e.g., drain station) that produces more effective fluid dynamical behavior, such as controlled fluid-to-structure interaction and jet-to-probe impingement interaction for probe drying operations. In particular, it is desired that a fluid flow is created in the upper portion of the rinsing well so that the above-mentioned problems of spitting and/or carryout are minimized or eliminated.

These and other aspects and features of the invention will be described with reference to FIGS. 3A-7B herein.

Figure 3A:
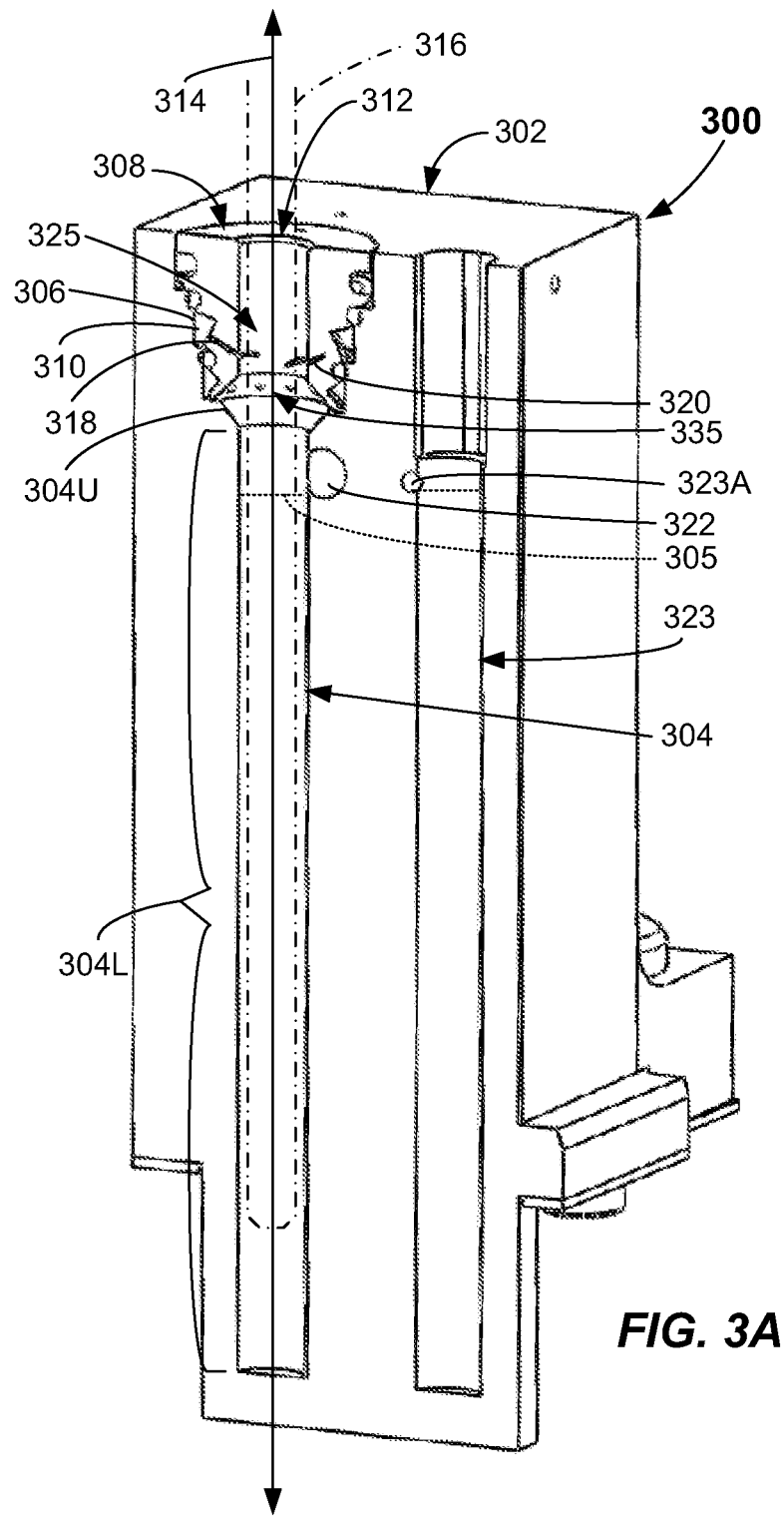
FIG. 3A is a cross-sectioned perspective view of a rinsing and drying apparatus according to embodiments of the present invention.
Figure 3B:
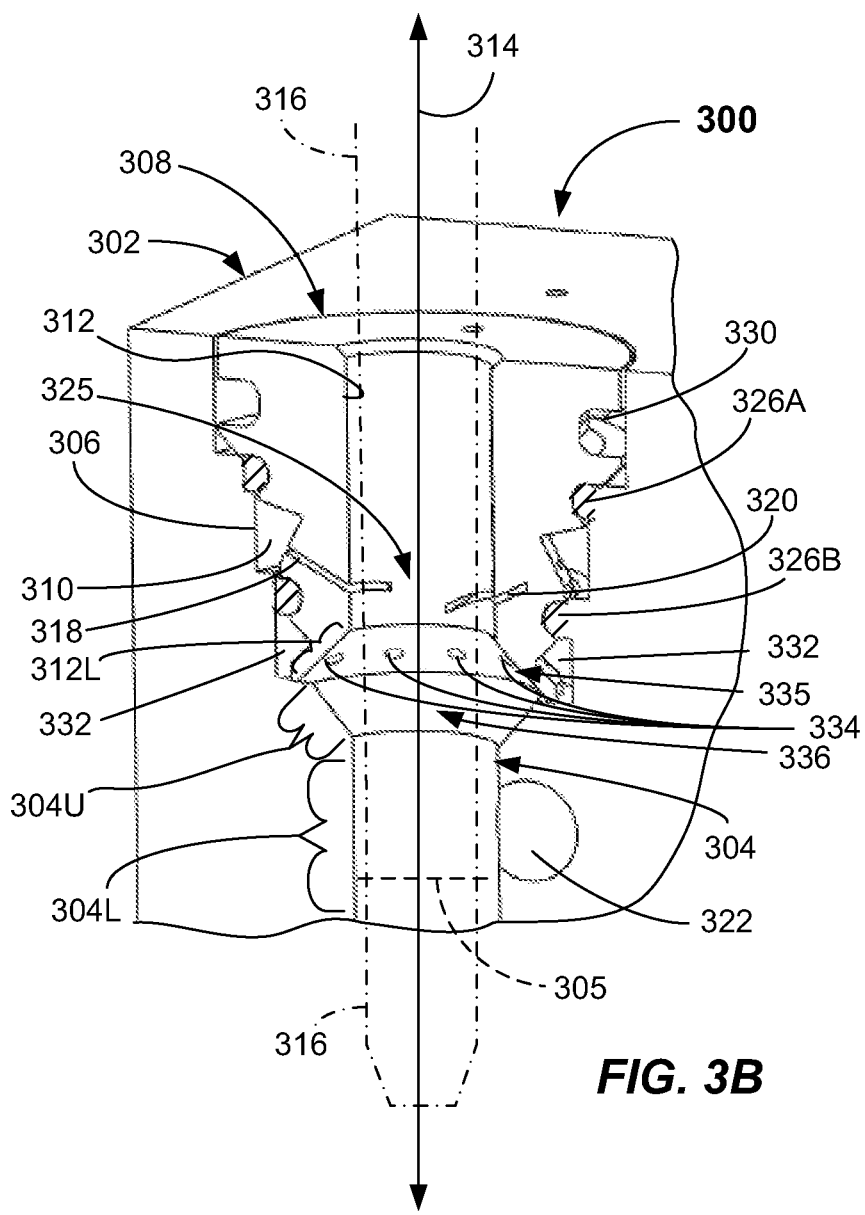
FIG. 3B is a partial cross-sectioned perspective view of a nozzle insert received in a nozzle recess according to embodiments of the rinsing and drying apparatus of the present invention.
Figure 3C:
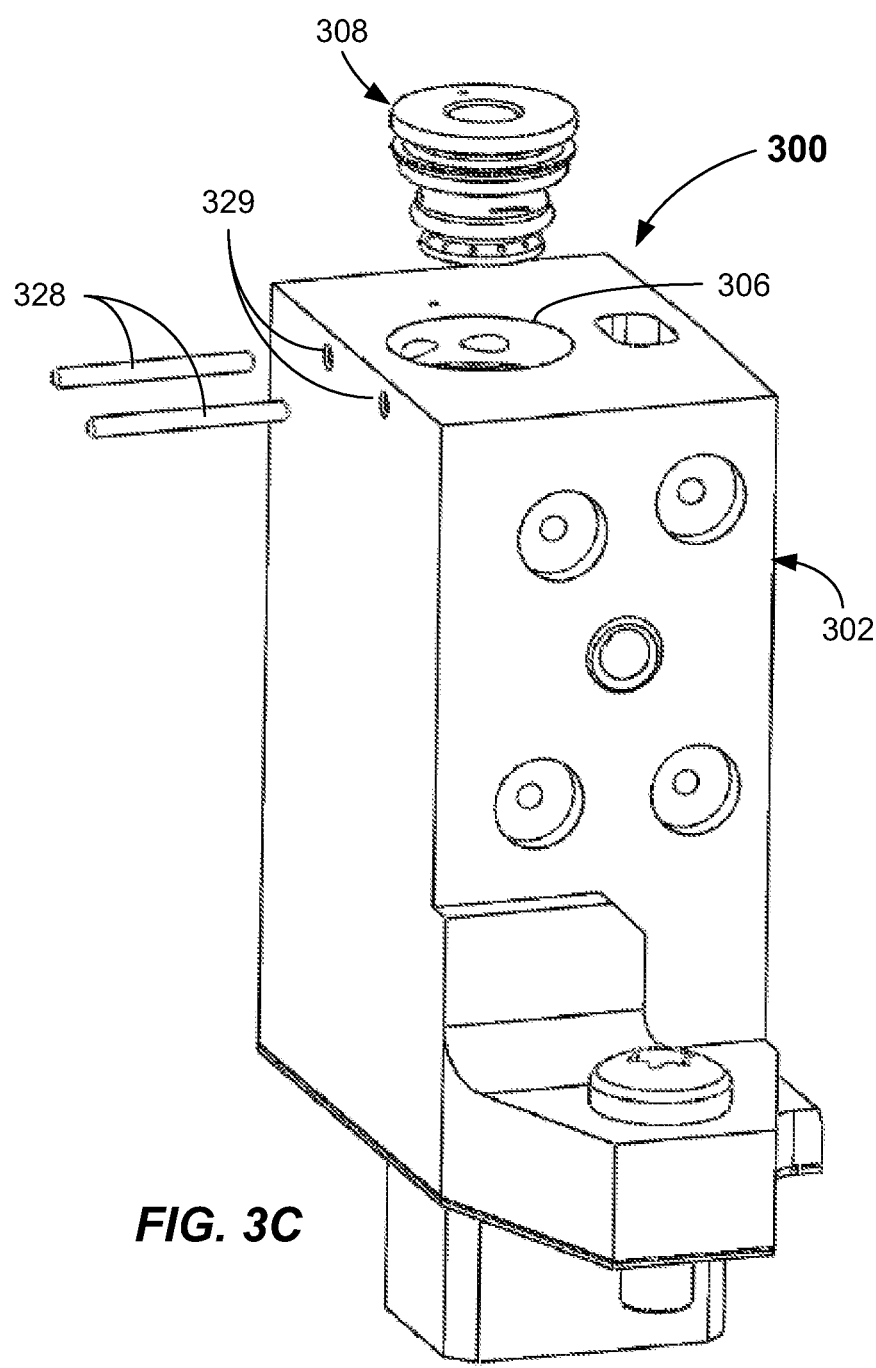
FIG. 3C is an exploded perspective view of the rinsing and drying apparatus of FIG. 3A.
Figure 3D:
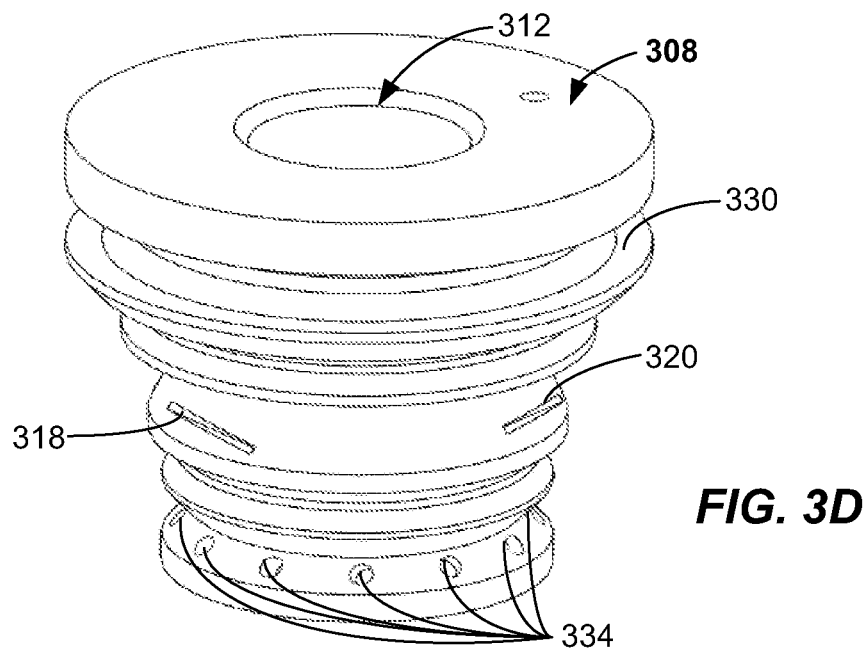
FIG. 3D is a perspective view illustrating a nozzle insert according to embodiments of the present invention.
Figure 3E:
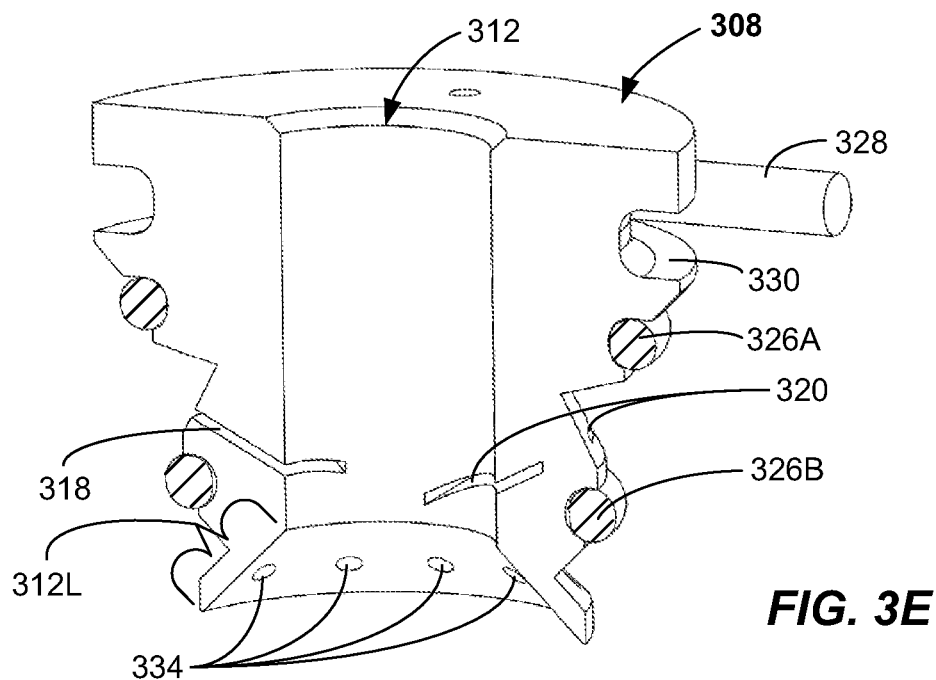
FIG. 3E is a cross-sectioned perspective view illustrating the nozzle insert of FIG. 3D.

Referring now to FIG. 3A, an improved rinsing and drying system 300 is illustrated according to embodiments of the invention. The invention provides improved geometry of the upper portion of the rinsing well and/or of the air-knife feature that may enable relatively more efficient execution of the final drying step of the rinsing and drying sequence. The reservoir geometry within the upper portion of the rinsing well and the improved geometry/configuration of the air-knife feature of the present invention improve the overall fluid dynamics and fluid-structure interaction to enable relatively more effective probe drying, as well as direct removal of all liquids and other material to a vacuum exhaust port.

More specifically, to generate reliable fluid-structure interaction for probe-drying operations (planar jet-to-probe impingement) and stabilized internal fluid dynamics (e.g., little or no recirculation) for an improved rinsing and drying apparatus, specific geometrical features were developed. In a first aspect, a group of two or more nozzles (e.g., inclined nozzles) are oriented with a horizontal offset from a longitudinal axis of a probe passage that is adapted to receive the sample probe. In a second aspect, the probe passage shape is improved. In another aspect, a shape of the reservoir below the probe passage is improved. One or more of these features may produce improved dynamic fluid motion that functions to produce a relatively more stable swirling flow field and improve the gas-jet wiping of the liquid from the probe for effective sample probe drying.

Referring now to FIGS. 3A-3N, an embodiment of the present invention will now be described. According to an aspect of the invention, a sample probe rinsing and drying apparatus 300 is provided. The sample probe rinsing and drying apparatus 300 includes a drain station body 302 defining a rinsing well 304 adapted to contain a rinsing liquid 305 (depth of the rinsing liquid 305 shown dotted), and a nozzle recess 306. The nozzle recess 306 may include a number of steps at different diameters. The drain station body 302 may be manufactured from any suitable polymeric material, such as an acrylic material. Other suitable materials may be used. A nozzle insert 308 is received in the nozzle recess 306, and the structure of the nozzle insert 308 and recess 306 cooperate to form a first annulus 310. The nozzle insert 308 has a probe passage 312 formed along, and preferably centered on, a longitudinal axis 314. The probe passage 312 is adapted to receive a sample probe 316 therein (sample probe 316 shown in phantom lines). The apparatus 300 further includes at least two nozzles 318, 320 having entries 318A, 320A, at the first annulus 310 and exits 318B, 320B at the probe passage 312. Each of the nozzles 318, 320 includes a central axis 318C, 320C located at the geometrical center thereof that is offset from the longitudinal axis 314 in a horizontal direction 321A (See FIG. 3H). The nozzles 318, 320 and the first annulus 310 make up the air knife feature 325.

In the depicted embodiment, the rinsing well 304 includes a lower well portion 304L having a substantially cylindrical shape; the lower well portion 304L extending in an orientation that is substantially vertical and substantially parallel with the longitudinal axis 314. The rinsing well 304 may include an upper well portion 304U below the nozzle recess 306, having at least a portion that has a larger transverse dimension than a transverse dimension (e.g., diameter) of the lower well portion 304L. In the depicted embodiment, the upper well portion 304U has a frustoconical shape providing a smooth transition to the substantially cylindrical lower well portion 304L. In the illustrated embodiment, an exhaust port 322 is coupled to the lower well portion 304L just below the upper well portion 304U (see FIG. 3B). The exhaust port 322 has a central axis 322C that may be oriented substantially tangentially to an outer wall of the lower well portion 304L as shown in FIGS. 3A, 3B, and 3F-3I.

The drain station body 302 may also include a cleansing well 323 that is positioned next to the rinsing well 304 and may contain a cleansing liquid. A cleansing well exhaust port 323A may be provided adjacent to the cleansing well 323. As with the exhaust port 322, the exhaust port 323A is used to evacuate used cleansing fluid and control the cleansing bath level.

Figure 3F:
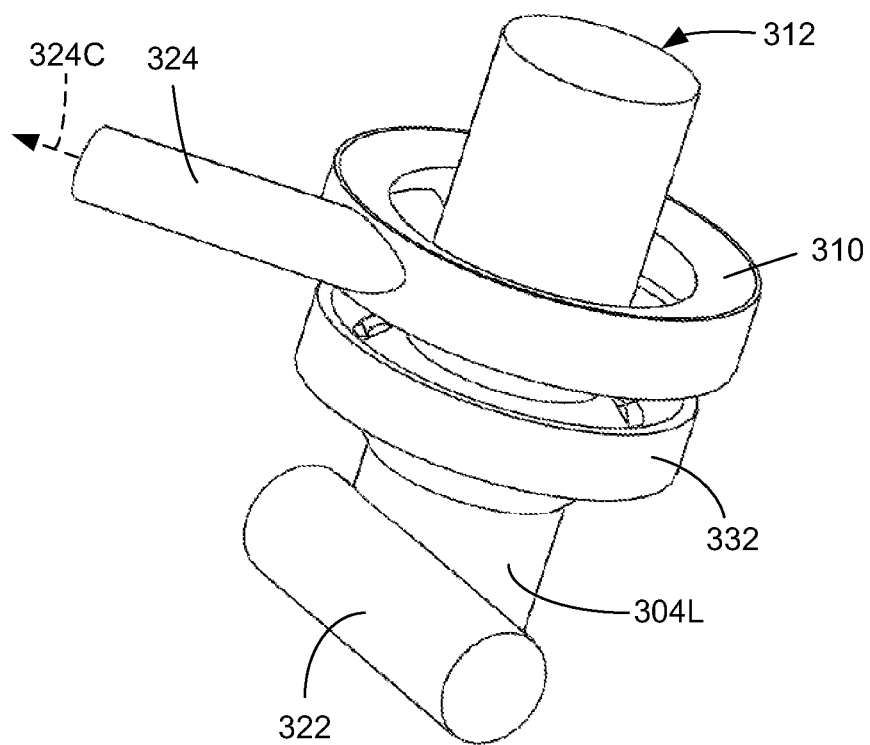
FIG. 3F is a perspective view diagram of the fluid-containing passages and cavities of the improved sample probe rinsing and drying apparatus according to embodiments of the invention.
Figures 3G, 3H:
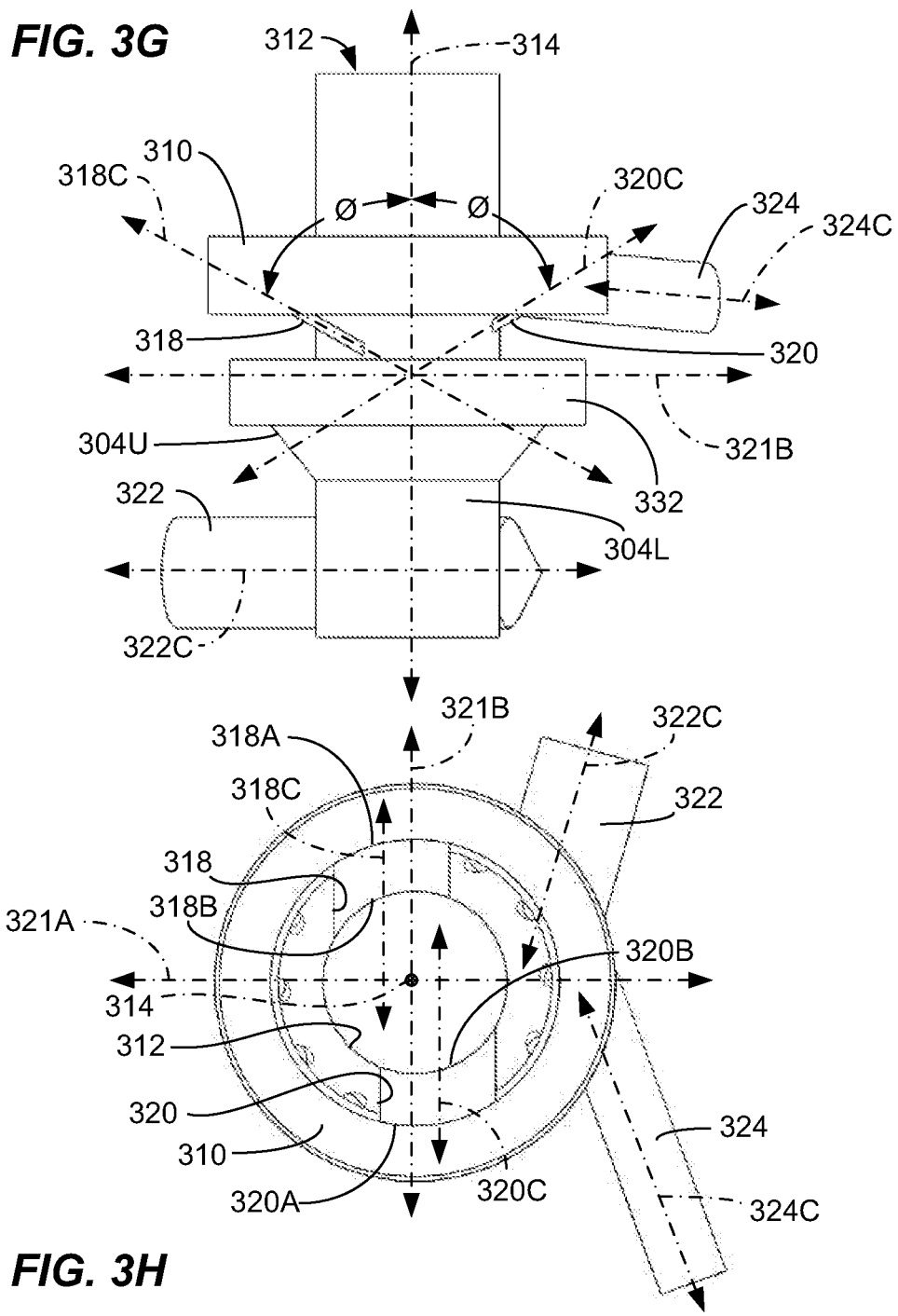
FIG. 3G is a side view diagram of the fluid-containing passages and cavities of the improved sample probe rinsing and drying apparatus of FIG. 3A.
FIG. 3H is a top view diagram of the fluid-containing passages and cavities of the improved sample probe rinsing and drying apparatus of FIG. 3A.

In more detail, each nozzle 318, 320 may be configured in a downwardly-angled orientation from the entries 318A, 320A with the central axis 318C, 320C of each nozzle 318, 320 being nonparallel with a substantially horizontal second axis 321B that is perpendicular to the longitudinal axis 314 as shown in FIGS. 3G and 3H and also perpendicular to horizontal axis 321A shown in FIG. 3H. For example, the angle ø between the longitudinal axis 314 and each respective central axis 318C, 320C may be between about 30 degrees and 75 degrees, or even between about 45 degrees and 75 degrees, for example. Preferably, the angle ø for each nozzle 318, 320 is about equal. Other angles may be used. At the exits 318B, 320B of the nozzles 318, 320, the probe passage 312 may be substantially cylindrical. In the depicted embodiment, the first annulus 310 comprises a cylindrical annulus. The cross-sectional shape of the annulus 310 may be square, rectangular, triangular, round, half round, or of other polygonal shapes. In the depicted embodiment, a v-shaped point is provided on the inner portion of the first annulus 310. The nozzles 318, 320 are preferably rectangular in cross section and have a width of about 2 mm to about 4 mm and a thickness of about 0.1 mm to about 0.3 mm in cross section.

In the depicted apparatus 300, the fluid inlet port 324 to the annulus 310 has a central axis 324C that is oriented substantially tangential to the annulus 310 (See FIGS. 3F-3H). In this way, the pressurized fluid is provided into the annulus 310 with relatively low fluid restriction. The nozzle insert 308 may also include first and second o-rings 326A, 326B received in grooves positioned above and below the annulus 310 (See FIG. 3B). The nozzle insert 308, which may be manufactured from a titanium material or other corrosion-resistant material, may be inserted into the nozzle recess 306 in the drain station body 302. The nozzle insert 308 may be retained in the nozzle recess 306 by pins 328 received through holes 329 and engaged with upper groove 330 (See FIGS. 3C and 3E). Pins 328 may be secured in holes 329 by a press fit or otherwise retained in holes 329 by mechanical fasteners, set screws, adhesive, weld, etc.

The rinsing and drying apparatus 300 may include a second annulus 332 positioned below the first annulus 310. The second annulus 332 may be formed by the cooperation of the geometry of the nozzle insert 308 and the nozzle recess 306 (FIG. 3A). The second annulus 332 is fluidly coupled to a plurality of shower passages 334 extending from the second annulus 332 to a lower portion 312L of the probe passage 312 at a lower portion of the nozzle insert 308 (see FIG. 3B). The plurality of shower passages 334 and second annulus 332 make up the shower feature 335. The lower portion 312L may include a frustoconical portion. As installed, the upper portion of the rinsing well 304 and the lower portion 312L of the probe passage 312 may cooperate to form a reservoir 336 into which the shower of rinsing liquid from the shower feature 335 may be directed. In the depicted embodiment, opposed frustoconical portions 312L, 304U form the reservoir 336. However, other circular reservoir shapes without sudden expansion may be used. The frustocone angle should be no greater than about 45 degrees from the longitudinal axis 314, for example.

Figure 3I:
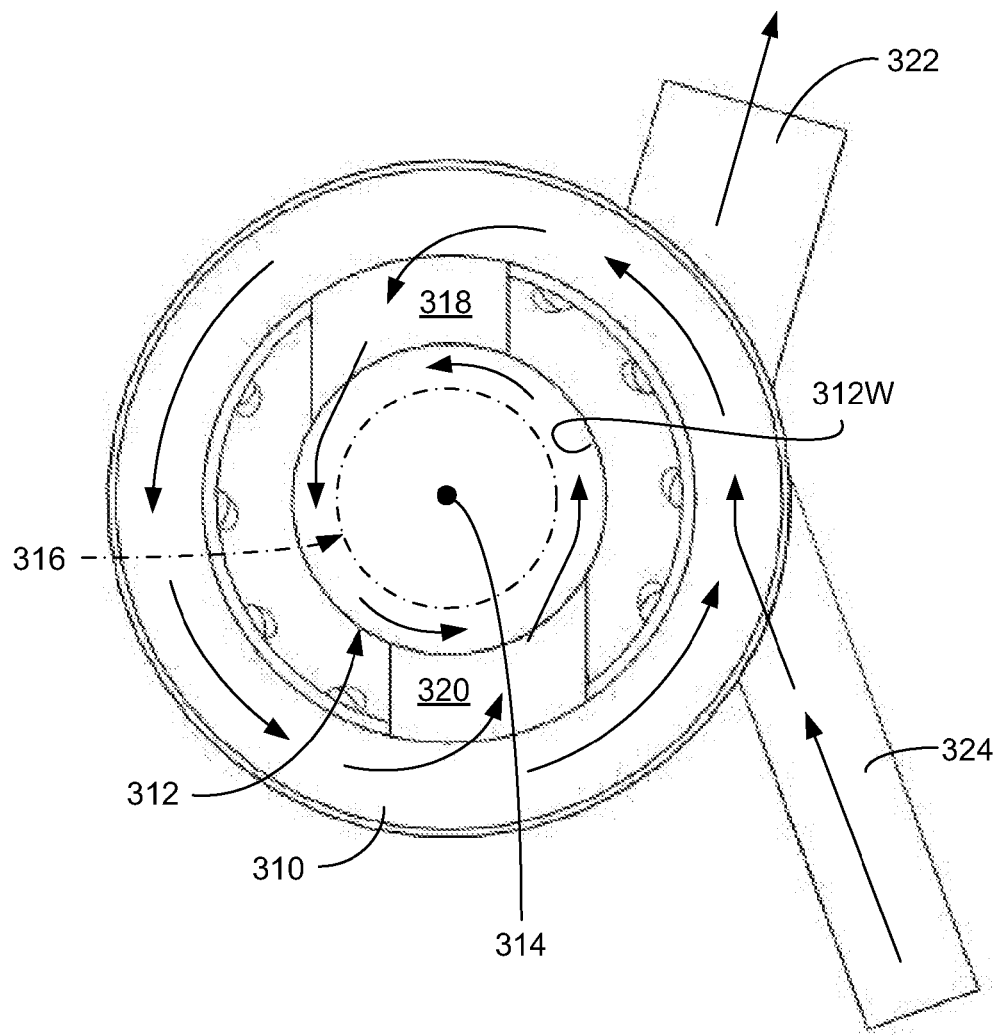
FIG. 3I is a top view diagram of the flow patterns within the fluid-containing passages and cavities of an embodiment of the sample probe rinsing and drying apparatus of the invention.

FIG. 3I illustrates implementation of a swirling flow path produced around the sample probe 316 (shown in phantom lines) according to aspects of the invention. The geometry of the probe passage 312 may be generally cylindrical at the nozzle exits, and the fluid (e.g., air) may be introduced into the space between the outer wall 312W of the probe passage 312 and the sample probe 316 by the first and second nozzles 318, 320. The nozzles 318, 320 may be oriented to provide for fluid-jet trajectories that are generally tangential to the cylindrical wall 312W of the probe passage 312. The jets from the nozzles 318, 320 are not directly opposed, but are offset (e.g., equally offset) from the longitudinal axis 314 (shown as a dot) to cause the flows from each to swirl, interleave, and follow roughly parallel helical paths. As the fluid (e.g., air) exits the nozzles 318, 320, a portion of each fluid jet impinges onto the sample probe 316, while the remaining portion of each jet contributes mutually to the generation of a generally stable, swirling flow field around the sample probe 316. Thus, the fluid flow has relatively high momentum and entrains any liquid on the surface of the sample probe 316 and any surrounding liquid (e.g., any liquid on the wall surface 312W of the passage 312). A vacuum from a vacuum source 510 (FIG. 5) is applied at the exhaust port 322 to collect and exhaust any liquid or other material swept from the sample probe 316 and walls 312W.

For example, the fluid (e.g., air) flow generally tangentially enters the first annulus 310 from the fluid inlet port 324 and may circle around the annulus 310 in a counterclockwise direction, for example. The fluid may then enter into the nozzles 318, 320 at their respective entries and then exit at their respective exits into the space between the wall 312W and the sample probe 316. Within the space, the fluid flow is swirling around the probe 316 at a relatively high rate of speed. The fluid (e.g., air) velocity in the space may be between about 10 m/s and about 50 m/s, for example. The flow rate may be about 10 to 20 liters per minute, for example. To the extent that the nozzles 318, 320 may include a downward orientation at their exits, the fluid flow may be both swirling about the sample probe 316, and also downwardly oriented to produce a generally helical flow pattern.

Figure 4:
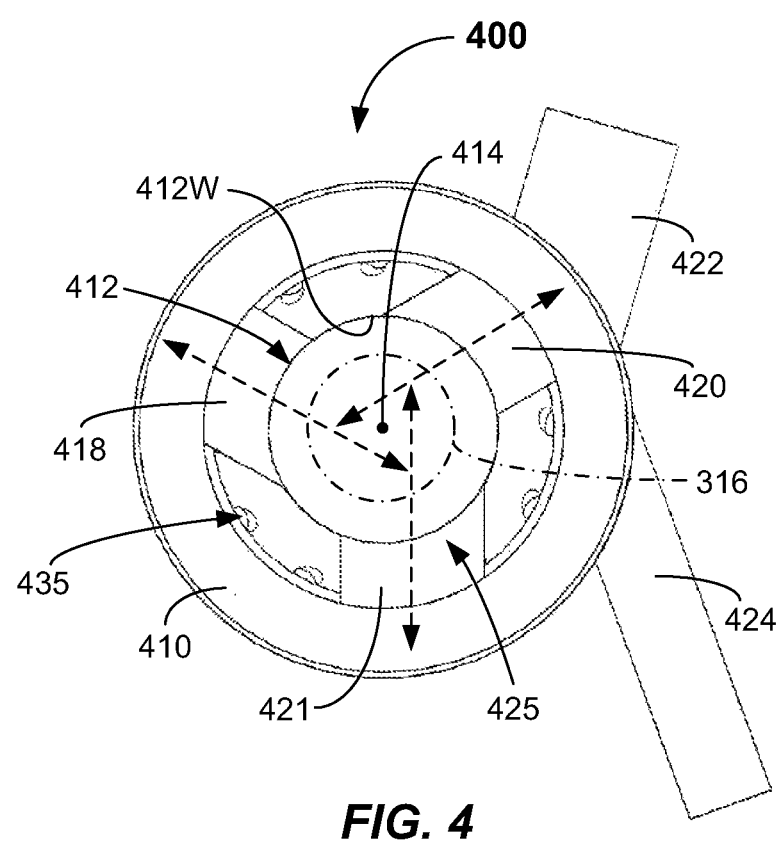
FIG. 4 is a top view diagram of fluid-containing passages and cavities of another embodiment of a sample probe rinsing and drying apparatus.

FIG. 4 illustrates another embodiment of a rinsing and drying apparatus 400 according to aspects of the invention. The geometry of the probe passage 412, first annulus 410, inlet port 424, and exhaust port 422 are the same as before described. However, this embodiment includes three nozzles 418, 420, 421 that may be oriented to provide for fluid-jet trajectories that are generally tangential to the cylindrical wall 412W of the probe passage 412. As before, the central geometrical axes of each of the jets from the nozzles 418, 420, 421 are not directly opposed, but are offset (e.g., equally offset) from the longitudinal axis 414 (shown as a dot) to cause the flows from each nozzle to swirl, interleave, and follow roughly parallel helical paths. As the fluid (e.g., air) exits the nozzles 418, 420, 421, a portion of each fluid jet impinges onto the sample probe 316, while the remaining portion of each jet contributes mutually to a generally stable, swirling flow field around the sample probe 316. Thus, the function is as heretofore described. Each of the nozzles 418, 420, 421 may be downwardly oriented as above described and, thus, may impart a substantially helical flow trajectory around the probe 316.

Figure 5:
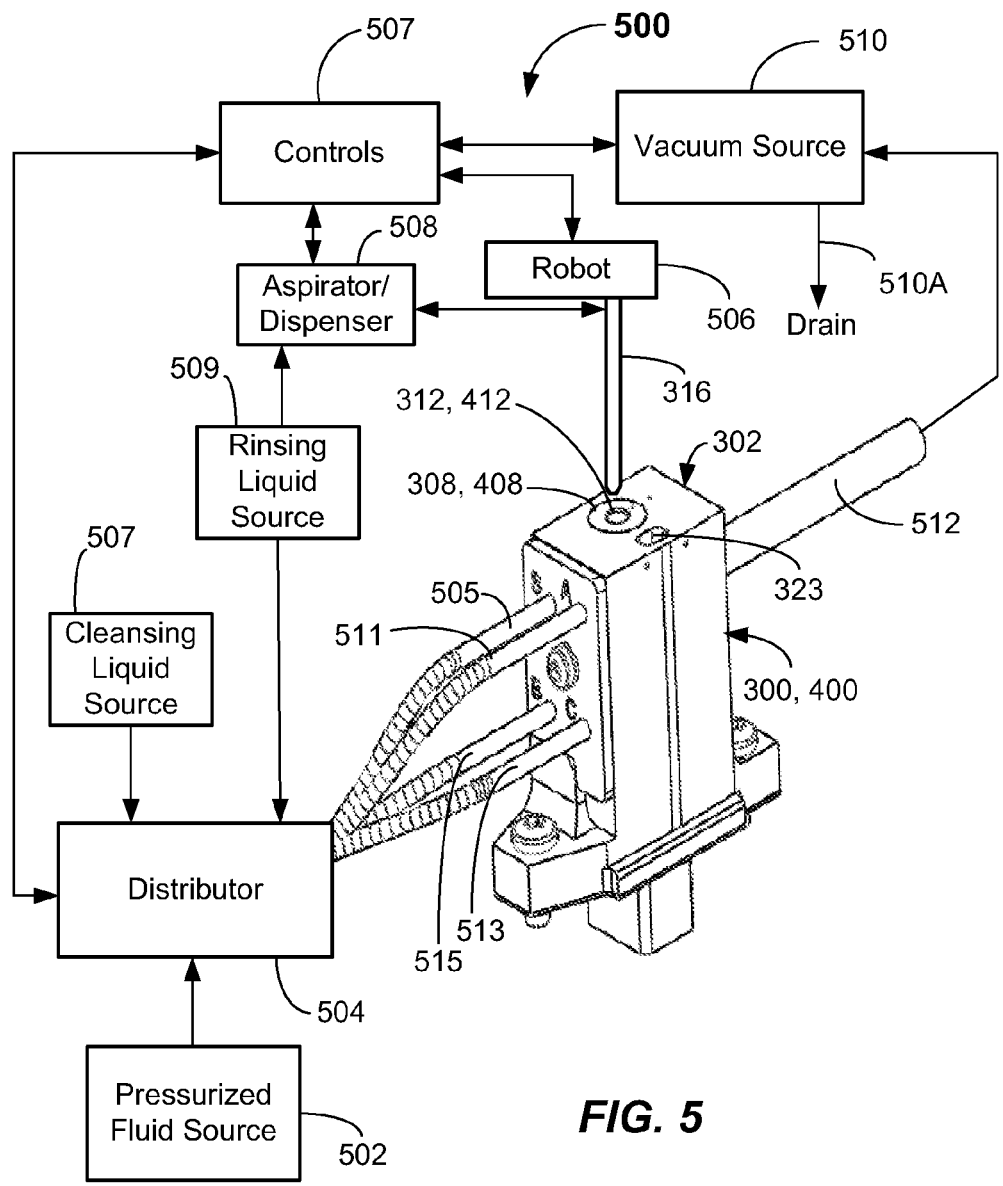
FIG. 5 is a left side perspective view of a rinsing and drying system according to embodiments of the present invention.

Now referring to FIG. 5, a rinsing and drying system 500 according to another aspect of the invention is disclosed. The system 500 includes a pressurized fluid source 502, such as pressurized air. The air may be provided at a pressure of about 20 psi, for example. Other pressures may be used. Suitable conduits may connect to a distributor 504 and, thus, pressurized air may be provided to the air-knife feature 325, 425 (see FIGS. 3B and 4) of the rinsing and drying apparatus 300, 400 in conduit 505. The distributor 504 may be a suitable series of valves and passages adapted to selectively cause flow of the fluids and liquids to the various annulus and wells. The system 500 includes a drain station body 302, and a nozzle insert 308, 408 as described above. As also before described, the nozzle insert 308, 408 includes a probe passage 312, 412 adapted to receive the sample probe 316.

In operation, the system 500 may include any suitable moving component(s) such as robot 506 for carrying out motion of the sample probe 316. The robot 506 may include suitable robot components (e.g., one or more robot arms, beams, or gantries) to which the sample probe 316 may be mounted. Suitable motion may be imparted to the probe 316 by the robot 506, such as one-axis, two-axis, or three-axis motion. The robot 506 may be actuated by commands from suitable controls 507.

In one embodiment, the sample probe 316 is first moved above and lowered into, and is at least partially immersed in, a cleansing well 323 by robot 506. While immersed in the cleansing well 323, the aspirator/dispenser 508 may draw some of the cleansing liquid into the interior of the probe 316 to cleanse same. Aspirator/dispenser 508 may be adapted, and operational, to control a level of pressure to draw in a desired amount of the sample fluid, reagent, cleansing liquid, etc. into the probe 316, and also to control the dispensing operations performed by the probe 316. The aspirator/dispenser 508 may include suitable pressure sensor(s), valve(s), accumulator(s), or other pneumatic or hydraulic components (not shown) to effectuate the liquid aspirating/dispensing action. Any suitable apparatus for drawing the fluid into the probe 316 may be used. For example, aspirating and dispensing systems that may be used with the present invention are described in U.S. Pat. Nos. 7,634,378; 7,477,997; and 7,150,190, which are hereby incorporated by reference herein. After cleansing the tip, the sample probe 316 may be withdrawn to the position of the exhaust port 323A (FIG. 3A), and the cleansing liquid may be dispensed by aspirator/dispenser 508 into the exhaust port 323A. The used cleansing liquid may then be exhausted in conduit 512 to a drain 510A, for example. After cleansing, the cleansing liquid may be replenished from cleansing liquid source 507 through distributor 504 and conduit 513.

Following cleansing, the sample probe 316 may be moved above and lowered by the robot 506 through the probe passage 312, 412 and into the rinsing well 304 (FIG. 3A). The sample probe 316 may be either centrally located or slightly misaligned in the probe passage 312, 412. In some embodiments, when the tip of the probe 316 is positioned adjacent to the exhaust port 322, rinsing liquid from rinsing liquid source 509 may be dispensed by aspirator/dispenser 508 to rinse the interior of the probe 316. The vacuum source 510 evacuates the used rinsing liquid into exhaust port 322 through conduit 512 and to drain 510A. In some embodiments, the shower feature (e.g., 335, 435) of the apparatus 300, 400 may be employed to receive rinsing liquid in conduit 511 from rinsing liquid source 509 and distributor 504 to rinse an exterior of the probe 316 as the probe 316 enters or is withdrawn from the probe passage 312, 412. Suitable conduits 515, 513 may provide supplies of rinsing liquid and cleansing liquid from rinsing liquid source 509 and cleansing liquid source 507, respectively, to the bottoms of the rinsing and cleansing wells 304, 323 (See FIG. 3A).

After the probe 316 is rinsed, the probe 316 may be withdrawn from the rinsing well 304 and a flow of fluid (e.g., air) is provided in conduit 505 from pressurized fluid (air) source 502 through distributor 504 and conduit 505 to produce swirling fluid jets (e.g., air jets) onto the exterior of the probe 316. During the fluid-jet (e.g., air-jet) drying operation, the fluid dynamics are substantially that of a turbulent swirling (helical) flow in the annular space between the probe 316 and the walls of the probe passage 312, 412. Fluid motion during an idle mode of operation is also substantially stable; following a substantially direct trajectory from the probe passage 312, 412 to the exhaust port 322 with substantially little or no fluid-vortex (e.g., air-vortex) recirculation or rinsing liquid up-wash.

Figure 6:
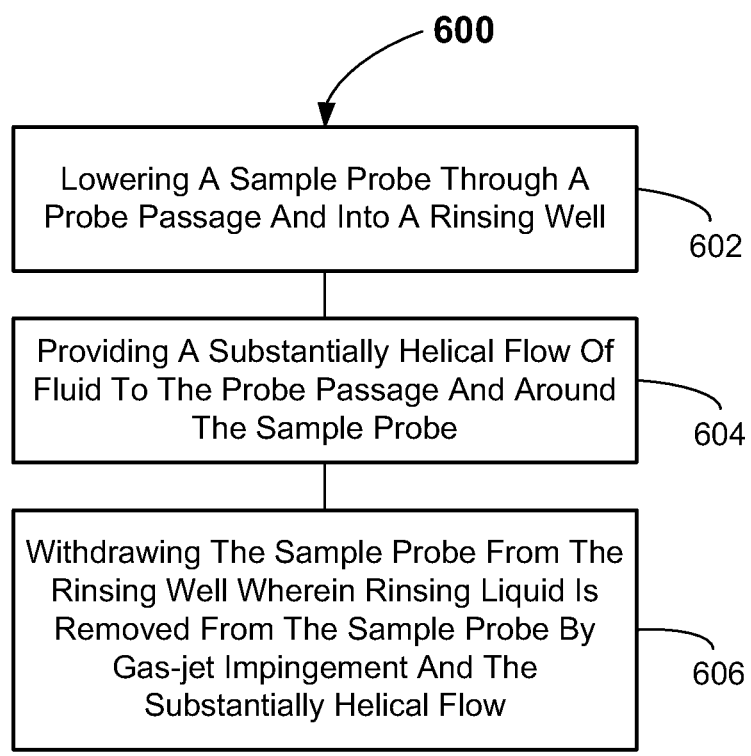
FIG. 6 is a flow chart illustrating a method according to embodiments of the present invention.

Thus, in summary, the method of rinsing and drying a sample probe includes, as best represented in FIG. 6, lowering the sample probe through a probe passage and into a rinsing well in 602, providing a substantially helical flow of fluid to the probe passage and around the sample probe in 604, and withdrawing the sample probe from the rinsing well wherein rinsing liquid is removed from the sample probe by gas-jet impingement and the substantially helical flow in 606.

Figure 7A:
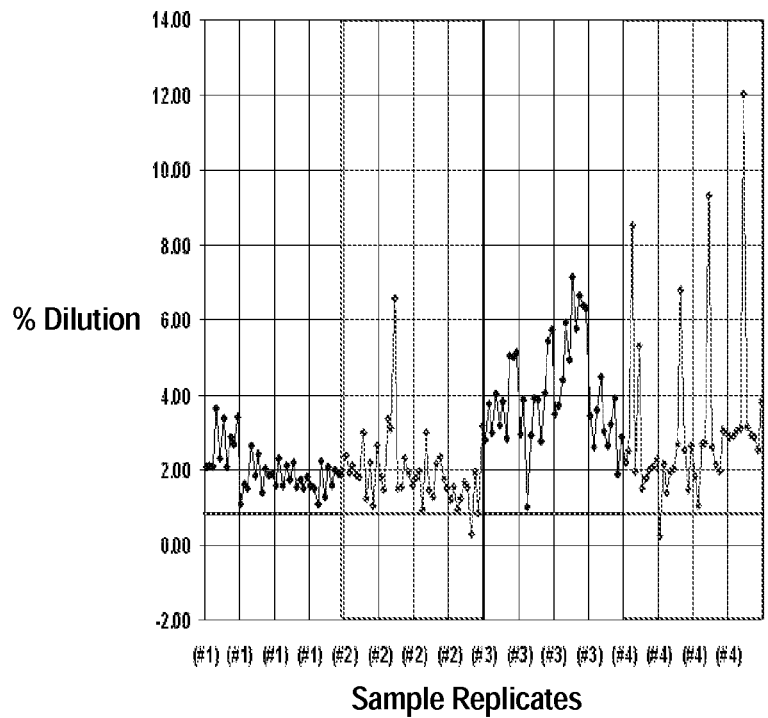
FIG. 7A is a graph illustrating performance of a method according to the prior art.

FIG. 7A is a graph illustrating performance of a method according to the prior art. More specifically, the graph represents a plot of % Dilution vs. Sample Replicates. The scattered and somewhat randomly distributed analytical results show that the behavior of rinsing liquid droplet trajectories and deposition onto the sample probe using conventional methods is typically unpredictable and includes wide disparities in % Dilution from test to test. Additionally, the illustrated % Dilution is nominally between about 2% and about 6%.

Figure 7B:
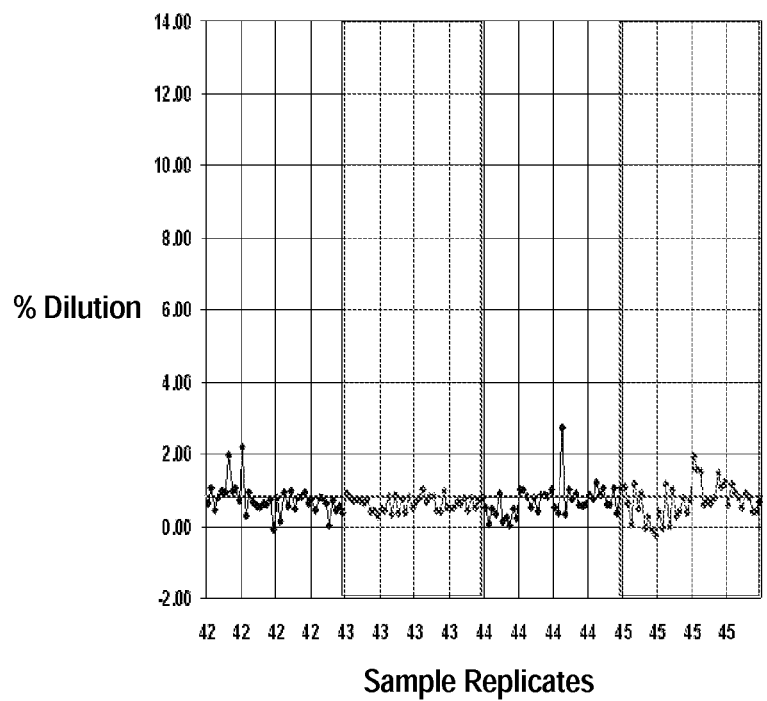
FIG. 7B is a graph illustrating a performance of a method according to embodiments of the present invention.

In operation, the described apparatus 300, 400 and system 500 produces a significant reduction in the unpredictable behavior of rinsing liquid droplet trajectories and deposition, which is reflected in more even and narrowly distributed analytical results (See FIG. 7B). Observed impact in controlled experiments is illustrated by the data in FIG. 7B, which illustrates a plot of % Dilution vs. Sample Replicates. As is shown, sample/reagent dilution is reduced by up to about 15 times as compared to the prior art and, as a result, precision is increased by at about least 2 times. In particular, the % Dilution utilizing the improved apparatus 300, 400 and system 500 including a generally helical flow and improved air knife is dramatically reduced to a nominal % Dilution ranging between about 0.5% and about 1%. Moreover, the effect on % Dilution is amplified by the fact that most clinical analyzers may have multiple sample-reagent drains.

The present invention may be advantageously utilized in connection with clinical analyzers, and is particularly useful for those having a semi-flexible sample probe that may require adequate rinsing passage clearance to accommodate uncertainty in robotic positioning. As will be appreciated, the present invention accommodates for probe offset in addition to producing a stable, generally helical flow field that improves probe drying.

Having shown the preferred embodiment, those skilled in the art will realize many variations are possible that will still be within the scope and spirit of the claimed invention. Therefore, it is the intention to limit the invention only as indicated by the scope of the claims.

What is claimed is:

1. A sample probe rinsing and drying apparatus, comprising:
   a drain station body defining a rinsing well adapted to contain a rinsing liquid, and defining a nozzle recess having an inner wall;
   a nozzle insert received in the nozzle recess and proximate the inner wall to form a first annulus, the nozzle insert having
      a probe passage formed along a longitudinal axis, the probe passage adapted to receive the sample probe therein, and
      at least two nozzles formed in the nozzle insert and having entries at the annulus and exits at the probe passage, each of the at least two nozzles having a central axis that is horizontally offset from the longitudinal axis; and a second annulus below the first annulus, and a plurality of shower passages extending from the second annulus to the probe passage at a lower portion of the nozzle insert.

2. The rinsing and drying apparatus of claim 1, wherein the rinsing well comprises:
a lower well portion having a substantially cylindrical shape, the lower well portion extending in an orientation that is substantially vertical and substantially parallel with the longitudinal axis, and an upper well portion below the nozzle recess having a frustoconical shape.

3. The rinsing and drying apparatus of claim 1, further comprising each nozzle being provided in a downwardly angled orientation from the entries to the exits into the rinsing well with the central axis of each nozzle being nonparallel with a substantially horizontal axis perpendicular to the longitudinal axis.

4. The rinsing and drying apparatus of claim 3, further comprising each nozzle being provided at an angle θ to the longitudinal axis of between about 30 degrees and 75 degrees.

5. The rinsing and drying apparatus of claim 1, wherein the probe passage comprises a cylinder at the exits of the nozzles.

6. The rinsing and drying apparatus of claim 1, wherein the first annulus comprises a cylindrical annulus.

7. The rinsing and drying apparatus of claim 1, comprising a fluid inlet port to the first annulus having a central axis that is oriented substantially tangential to the first annulus.

8. The rinsing and drying apparatus of claim 1, comprising first and second o-rings positioned in grooves above and below the first annulus.

9. The rinsing and drying apparatus of claim 1, wherein the plurality of shower passages extend from the second annulus to a frustoconical portion of the probe passage.

10. The rinsing and drying apparatus of claim 1, comprising an exhaust port coupled to a lower well portion, the exhaust port having a central axis that is oriented substantially tangential to the lower well portion.

11. A rinsing and drying system, comprising:
a pressurized fluid source comprising gas;
a drain station body defining a rinsing well and nozzle recess; and
a nozzle insert received in the nozzle recess proximate to an inner wall, the inner wall and the nozzle configured to form a first annulus, the nozzle insert having
a probe passage formed along a longitudinal axis adapted to receive a sample probe therein, and
at least two nozzles in the nozzle insert having entries at the first annulus and exits at the probe passage, each of the at least two nozzles being oriented and configured to direct a flow of fluid comprising gas into the probe passage,
wherein a portion of each flow of fluid comprising gas from the nozzles contacts the probe and the remaining portion of each flow of fluid together form a substantially helical flow field within the probe passage.

12. The rinse and drying system of claim 11, further comprising each nozzle being provided in a downwardly angled orientation from the entries to the exits with the central axis of each nozzle being nonparallel with a substantially horizontal axis perpendicular to the longitudinal axis.

13. The rinse and drying system of claim 11, wherein a central axis of each nozzle is horizontally offset from the longitudinal axis and the flow of fluid from each nozzle is directed in a substantially tangential pattern relative to an interior wall of the probe passage.

14. A sample probe rinsing and drying system, comprising:
a drain station body defining a rinsing well and nozzle recess;
a nozzle insert received in the nozzle recess proximate to an inner wall, the inner wall and the nozzle configured to form an annulus, the nozzle insert having
a probe passage formed along a longitudinal axis adapted to receive a sample probe therein, and
at least two nozzles in the nozzle insert having entries at the annulus and exits at the probe passage, each of the at least two nozzles being oriented and configured to direct a flow of fluid into the probe passage;
a pressurized fluid source comprising gas fluidly coupled to the annulus;
a rinsing solution source coupled to the rinsing well; and
a vacuum source coupled to the rinsing well,
wherein a portion of each flow of fluid comprising gas from the nozzles is operable to contact the sample probe and the remaining portions of each flow of fluid together form a substantially helical flow field within the probe passage.

15. A method of rinsing and drying a sample probe, comprising:
lowering the sample probe through a probe passage and into a rinsing well;
providing a substantially helical flow of gas to the probe passage and around the sample probe; and
withdrawing the sample probe from the rinsing well, wherein rinsing liquid is removed from the sample probe by gas-jet impingement and the substantially helical flow of the gas.

16. The method of claim 15, comprising showering the sample probe with a liquid from a shower feature.

17. The method of claim 15, comprising flushing rinsing liquid through the rinsing well.

18. The method of claim 15, comprising flushing rinsing liquid through an interior of the sample probe.

19. The method of claim 15, comprising:
lowering the sample probe into the cleansing well;
aspirating a cleaning solution into an interior of the sample probe; and
withdrawing the sample probe from the cleansing well.

20. A method of rinsing and drying a sample probe, comprising:
lowering the sample probe along a longitudinal axis of a probe passage and into a rinsing well including rinsing liquid;
providing a flow of fluid comprising gas into a substantially cylindrical annulus surrounding the probe passage;
directing the flow of fluid comprising gas from the substantially cylindrical annulus through at least two nozzles and into the probe passage and around the sample probe wherein the flow of fluid from each of the at least two nozzles has a central axis that is horizontally offset from the longitudinal axis; and
withdrawing the sample probe from the rinsing well, wherein the rinsing liquid is removed from the sample probe by impingement and gas-jet wiping by a substantially helical flow created by the offset.

* * * * *